United States Patent [19]

Packer et al.

[11] 4,438,279

[45] Mar. 20, 1984

[54] FIBER-GRADE TEREPHTHALIC ACID RECOVERED FROM THE EFFLUENT FROM PARAXYLENE OXIDATION IN ACETIC ACID AND THE CATALYTIC HYDROGENATION OF THE OXIDATION EFFLUENT IN THE PRESENCE OF METALLIC PLATINUM FAMILY METALS

[75] Inventors: Lawrence G. Packer, Lisle, Ill.; Edward J. Schlossmacher, Erie, Pa.

[73] Assignee: Standard Oil Company, a corporation of Indiana, Chicago, Ill.

[21] Appl. No.: 453,487

[22] Filed: Dec. 27, 1982

Related U.S. Application Data

[63] Continuation of Ser. No. 306,959, Sep. 30, 1981, abandoned.

[51] Int. Cl.$^3$ .................. C07C 51/16; C07C 51/42
[52] U.S. Cl. ........................... 562/416; 562/487
[58] Field of Search ............................. 562/487, 416

[56] References Cited

U.S. PATENT DOCUMENTS

| | | | |
|---|---|---|---|
| 3,546,285 | 12/1970 | Witt | 562/487 |
| 3,584,039 | 6/1971 | Meyer | 562/487 |
| 3,845,100 | 10/1974 | Kusak et al. | 562/416 |
| 4,197,412 | 4/1980 | Kimura et al. | 562/416 |

*Primary Examiner*—A. Siegel
*Attorney, Agent, or Firm*—Gunar J. Blumberg; William T. McClain; William H. Magidson

[57] ABSTRACT

Fiber-grade quality terephthalic acid can be obtained by dissolving partially purified terephthalic acid: the product separated from catalyst components and impurities in acetic acid solvent portion of oxidation effluent, acetic acid washed and dried: either in deionized water or acetic acid at temperatures from 250° C. and upward, contacting the solution and hydrogen gas with a hydrogenation catalyst preferably a platinum family metal disposed on an insoluble support followed by separation of the solution from catalyst, cooling the separated solution to precipitate terephthalic acid, recovering, washing and drying the precipitate. The use of deionized water in the purification route, with respect to the oxidative preparation of terephthalic acid, has the drawback of maintaining two distinctly different solvent systems and tolerating the rather limited water solubility of the p-toluic acid. While the use of acetic acid as solvent in the purification route makes use of a solvent having a greater capacity to dissolve p-toluic acid (an oxidation co-product impurity and the reduction product of 4-carboxybenzaldehyde also a co-oxidation product), such use of acetic acid has the drawback of decreasing the hydrogenation rate as well as having some inherent decomposition of the acetic acid solvent.

The aforementioned drawbacks are avoided by heating the oxidation effluent's suspension of impure solid terephthalic acid to a temperature of 250° C. and upward in the presence of sufficient acetic acid to dissolve all the solids of the total solids content of said effluent, contacting such solution and hydrogen gas with the above platinum family hydrogenation catalyst, then precipitating, recovering, acetic acid washing, and drying terephthalic acid so purified. Such purification and recovery route also provides a less yellow purified product than that produced when the same process is conducted but in the absence of the platinum family metal hydrogenation catalyst.

9 Claims, No Drawings

FIBER-GRADE TEREPHTHALIC ACID RECOVERED FROM THE EFFLUENT FROM PARAXYLENE OXIDATION IN ACETIC ACID AND THE CATALYTIC HYDROGENATION OF THE OXIDATION EFFLUENT IN THE PRESENCE OF METALLIC PLATINUM FAMILY METALS

This is a continuation of application Ser. No. 306,959, filed Sept. 30, 1981 now abandoned.

This invention relates to the production of high purity (e.g., fiber-grade) terephthalic acid by oxidation of p-xylene in acetic acid and the immediate catalytic hydrogenation of the resulting oxidation effluent, also in acetic acid. More specifically, the present invention pertains to the integration of the oxidation at a temperature of from 160° C. to 210° C. of liquid p-xylene with air in the presence of an acetic acid solution of ions of cobalt, manganese and bromine wherein there is present from 2.0 up to 14 weight parts of acetic acid solvent per 1.0 weight part of p-xylene and the catalytic hydrogenation at a temperature of from 260° up to 320° C. of the resulting oxidation effluent in the presence of sufficient acetic acid solvent to provide from 10 up to 30 grams of terephthalic acid solute for each 100 grams of solution in the presence of one of the platinum family metals in metallic form, preferably supported metallic form.

STATE OF THE ART BACKGROUND

The preparation of terephthalic acid by the air oxidation of liquid p-xylene in the presence of an acetic acid solution containing ions of bromine with cobalt and/or manganese ions was first disclosed in U.S. Pat. No. 2,833,816. But purification of terephthalic acid so produced by the catalytic hydrogenation of the oxidation effluent per se or diluted with acetic acid of from 0 up to 15 weight percent water so that all solids in the oxidation effluent dissolved at temperatures upward from 250° C. was first disclosed in early 1967 in British Patent Specification No. 1,056,319. Said purification by hydrogenation used 3.5 to 14 kg/cm$^2$ hydrogen partial pressure relied upon dissolved ions of cobalt and manganese to provide hydrogenation catalysis. The purified terephthalic acid, purified with respect to lowered 4-carboxybenzaldehyde (4-CBA) content, was recovered from the hydrogenated solution by recrystallization by cooling the solution to a temperature at least below the normal (760 mm Hg) boiling temperature of the solvent which was acetic acid containing from 3 up to 15 weight percent water. However, the tristimulus b-value color (a measure of yellowness indicated by a positive numerical value or of blueness indicated by a negative numerical value) of the purified terephthalic acid was not within the acceptable range of positive two to negative two, preferably positive one to negative one for fiber-grade quality terephthalic acid.

To be acceptable as fiber-grade terephthalic acid, that is a purified terephthalic acid acceptable for direct reaction with highly pure ethylene glycol in the manufacture of fibers from high molecular weight polyethylene terephthalate, the purified terephthalic acid had to have a purity of more than 99.9 weight percent and a 4-CBA content of 50 or less parts by weight per million (ppm) parts by weight of terephthalic acid in addition to the foregoing b-value color.

For the purified terephthalic acid to be used as an acceptable fiber-grade quality product from the standpoint of b-value color, total impurity and 4-CBA content, purification techniques other than those of the above British Patent Specification were needed. Such additional techniques included separating a partially purified terephthalic acid from the oxidation effluent by cooling it to a temperature of from 50° to 100° C. to maximize precipitation of terephthalic acid from solution, washing and drying the separated terephthalic acid. Such partially purified terephthalic acid was next dissolved in deionized water (U.S. Pat. No. 3,639,465) or in acetic acid containing from 0 up to 45 weight percent water (U.S. Pat. No. 3,546,285) at temperatures upward from 260° C. to provide a solution containing 10 to 30 weight percent terephthalic acid and based thereon from 500 up to 6,000 ppm of 4-CBA. The solution and hydrogen gas are next contacted with a noble metal (Group VIII) as catalyst and, after separating the treated solution from the catalyst, highly pure terephthalic acid as fiber-grade product was recovered by recrystallization, washed with fresh solvent and the washed product dried. In commercial application the partially purified terephthalic acid was collected in one or more storage silos before being redissolved in water to prepare the solution for catalytic hydrogenation. Also the dried fiber-grade product was collected in one or more silos before use of shipment.

The terephthalic acid recovered from the oxidation effluent is a "partially purified" product because its separation from reaction effluent's mother liquor leaves behind 50 to 65 percent of the co- and by-product impurities and components of catalysis in the effluent's mother liquor, adhering mother liquor is washed away, and even wash liquor is removed by drying.

We have conducted successfully for more than 15 years on a commercial basis the foregoing combination of p-xylene oxidation, recovery and storage of partially purified terephthalic acid, redissolution of the partially purified product in deionized water and the subsequent steps of catalytic hydrogenation through washing and drying to arrive at the fiber-grade terephthalic acid product.

We also investigated redissolving in fresh acetic acid the partially purified terephthalic acid followed by the catalytic hydrogenation, separation from catalyst, recrystallization washing and drying to obtain fiber-grade terephthalic acid. In these investigations the catalyst was metallic palladium (0.5 and 1.0 weight percent) disposed on the surface of high surface area per unit weight activated carbon, the hydrogen partial pressure was 7 kg/cm$^2$ and the hydrogenation temperature was 282° C. and 310° C. At the steady state conditions existing in a continuous flow process, using a 10 weight percent terephthalic acid solids content in predominantly acetic acid solvent, the 4-CBA concentration is about 150 ppm (dry basis) when using a 0.5 weight percent Pd catalyst at 282° C. 4-CBA concentrations in the purification reactor effluent when using a 1 percent Pd catalyst are respectively, 190 ppm and 245 ppm at temperatures of 282° C. and 310° C. Increasing the concentration of terephthalic acid from 10 weight percent to 20 weight percent, using a temperature of 310° C. and using a 1 percent weight Pd catalyst appears to reduce the 4-CBA concentration in the purification reactor effluent from 245 ppm to ~210 ppm. Said weight percent of terephthalic acid were the solutions concentrations and each partially purified terephthalic acid contained 3,000 ppm 4-CBA. In contrast the same partially purified terephthalic acid but dissolved in water at 20 weight percent of the solution had at steady-state conditions 277° C. and 7 kg/cm² hydrogen partial pressure a 4-CBA concentration of 70 ppm and 76 ppm of 4-CBA at 304° C. and 7 kg/cm² hydrogen partial pressure. Those 4-CBA concentrations were for the total solids in the hydrogenated solution, hence the total 4-CBA.

Even more discouraging was the fact that acetic acid could be catalytically decomposed. Under the most severe conditions of 310° C., when using a 20 weight percent terephthalic acid solution and catalyst of 1 weight percent palladium loading, total decomposition was determined to be 0.015 kg/kg terephthalic acid, and more terephthalic acid was converted to 4-CBA and p-toluic acid than when water was the reaction solvent. The acetic acid decomposition was mainly to carbon oxides, methane and ethane but analysis of the liquid phase showed acetaldehyde, acetone and methyl acetate as well as unknown products to be present.

Lastly, the publications of E. B. Maxted et al. concerning Catalytic Toxicity and Chemical Structure in the years 1937, 1938, and 1940 disclosed, based on the hydrogen gas reduction of N-crotonic acid at 25° C. in alcohol or acetic acid solution (10 ml.) and platinum (0.05-0.1 g) as catalyst, that many dissolved metals (in amounts between about 0.8 and about $1.6 \times 10^{-6}$ gram atoms) were tested for their toxic effect caused by being absorbed as layer or layers on the catalyst. The authors reported copper, silver and tin to have the same lowest deactivation of catalytic activity which for comparative purposes was assigned the relative effective toxicity of 1.0. With respect to the other metals tested their relative toxicities were compared to that of copper. Such toxicities were reported shown in Table I to follow which is from Table VI of the authors' 1940 publication.

TABLE I

| RELATIVE TOXICITIES OF METALS AGAINST PLATINUM AT 25° C. | |
|---|---|
| Metal | Relative Toxicity |
| Copper | 1.0 |
| Mercury | 1.7 |
| Thallium | 2.8 |
| Lead | 3.7 |
| Zinc | 4.0 |
| Cadmium | 4.0 |
| Nickel | 3.7 |
| Manganese | 4.0 |
| Iron | 4.1 |
| Cobalt | 5.1 |

Such 1940 reported test results confirmed earlier work of Paal et al. (Ber. 44, 46 and 51 in, respectively 1911, 1913, and 1918) that the metals copper, mercury, lead, zinc, cadmium deactivated platinum, and palladium catalysts when such metals were the support for said catalysts.

The foregoing toxicity facts concerning the relative toxicity of cobalt and manganese being, respectively, 3 and 2.4 times more toxic than mercury and even more toxic (cobalt being 1.38 more toxic) than lead and nickel appeared to indicate failure for our concept of using hydrogenation in the presence of palladium or platinum as catalyst of the p-xylene oxidation effluent as a step in the production of fiber-grade terephthalic acid.

However, in spite of the somewhat negative results obtained by the catalytic hydrogenation of fresh acetic acid solution of partially purified terephthalic acid and the apparent forecast of failure of our purification concept, we were indeed surprised with the success of an actual application of our inventive concept. We were able to decrease the 4-CBA content down to less than 50 ppm from 3,000 ppm, without excessive p-toluic acid appearing in the product and provide a product having a low b-color value below positive 1.0. Such results would not have been expected from a process whose hydrogenation step had present for each 0.1 gram of hydrogenation catalyst metal more than 10 times the amount of cobalt and more than 20 times the amount of manganese tested by Maxted et al. and found rather deactivating. Our amounts of cobalt and manganese and the amounts of the same metals tested by Maxted et al. per 0.1 gram hydrogenation catalyst metal are shown in Table II which follows.

TABLE II

| Gram-Atom $\times 10^{-6}$ of Cobalt and Manganese Per 0.1 Gram of Catalyst Metal | | | |
|---|---|---|---|
| Metal | Maxted et al. | Inventive Concept | Times Greater |
| Cobalt | 0.8 to 1.6 | 160 | 200 to 100 |
| Manganese | 0.8 to 1.6 | 320 | 400 to 200 |

The results of the example of the novel hydrogenation step of the present inventive concept will demonstrate, when measured against the results of the comparative example, that the presence of such gross amounts of cobalt and manganese during the platinum family metal catalyzed hydrogenation had little catalytic deactivating effect. Such amounts of cobalt and manganese may have offset the observed high p-toluic acid formation by over-hydrogenation of terephthalic acid as well as the high 4-CBA reduction floor (140 to 245 ppm total 4-CBA) when partially purified terephthalic acid was dissolved in fresh acetic acid and the solution hydrogenated in the presence of the platinum family metal catalyst.

SUMMARY OF THE INVENTION

The present inventive concept in its simplest form uses a platinum family metal catalyst in the recovery of purified terephthalic acid by the process of British Patent Specification No. 1,056,319 wherein the fluid effluent from the oxidation of p-xylene in acetic acid is heated to a temperature upward from 260° C. in the presence of sufficient acetic acid to dissolve all solids present in the effluent and in the presence of hydrogen gas followed by cooling the treated solution to precipitate terephthalic acid from solution, which when washed with fresh acetic acid and dried, is of fiber-grade purity. Thus the main difference between the present inventive concept and that of the foregoing Brisith Patent is the present inventive concepts use in the hydrogen treating step of a platinum family metal, more desirably platinum or palladium and preferably palladium, in the free metal form supported on the surface of an insoluble support. Such support, insoluble in the hot (260° C. and above) solution in acetic acid, is preferably activated carbon and more preferably is activated carbon of high ratio of surface area per unit weight. For example, the activated carbon support has a ratio of surface area per unit weight of from 1,000 to 3,000 square meters per gram.

Because of the foregoing difference the present terephthalic acid purification technique need not be limited to a final cooling temperature of from 177° C. down to 150° C. as were the purification processes of the British Patent mentioned above. Rather the final cooling temperature following separation of the treated solution from the catalyst can be down to as low as 20° C. to 25° C. However, for practical commercial application the final cooling can be down to a temperature in the range of from 120° to 90° C. Such cooling from 260° C. and above down to 120° to 90° C. can be accomplished by flash evaporation of solvent in two or more up to six to eight series-connected stirred crystallization zones operated at successively lower pressures.

Such flash evaporation of solvent conveniently permits ready removal of solvent as solute precipitates and no longer needs to be dissolved. Further, such flash evaporation of solvent also provides a distillative recovery of acetic acid solvent for re-use either as a hot vapor under pressure to be injected into the fluid oxidation reactor effluent to heat and, if necessary, to dilute it or to make use of its heat by indirect heat exchange.

The first vapors flashed while decompressing from the hydrogen free solution to the first crystallization pressure (e.g., from 38 kg/cm$^2$ to 25 kg/cm$^2$ gauge pressure) may, in addition to vapors of water and acetic acid, also contain vapors of p-toluic acid stripped from solution by the flashed vapors of water and acetic acid. Such hot pressurized mixture of vapors can better be used to heat either the oxidation effluent or a heat exchange fluid which can be used in a thermodynamic energy conversion (e.g., turbine) to provide mechanical energy for power generation or air compression. Thereafter, the cooled and further decompressed mixture can be used to provide direct heat to concentrate the mother liquor for its recycle to the oxidation as source of catalyst components and so that its oxidizable aromaticcontent (p-toluic acid and 4-CBA) can be with fresh p-xylene converted to additional terephthalic acid.

SPECIFIC EMBODIMENTS

The oxidation of p-xylene in acetic acid solution of components of catalysis can be conducted at a temperature in the range of from 130° C. up to 230° C. but more desirably is conducted at a temperature of from 170° C. up to 225° C. and a gauge pressure of from 2 up to 35 kg/cm$^2$ to maintain liquid phase conditions at said temperatures. The weight ratio of acetic acid solvent (3 to 5 weight percent water) to xylene can be in the range of from 2:1 up to 10:1. The components of catalysis can range from 0.4 up to 22 milligram atoms of cobalt per gram mole of p-xylene, a gram atom ratio of from 0.05:1.0 up to 2:1 milligram atoms of manganese per milligram atom of cobalt, and from 0.5:1.0 up to 1.5:1.0 milligram atoms of bromine per milligram atom of total of cobalt and manganese.

For example, there are used with each 1.0 gram mole of p-xylene 21.6 milligram atoms of cobalt, 1.08 milligram atoms of manganese and 32 milligram atoms of bromine for an oxidation of p-xylene wherein there are present six to ten weight parts of acetic acid per 1.0 weight part of p-xylene and the oxidation is conducted at a temperature of 170° C. to 190° C. with air as the source of molecular oxygen. Also for air oxidation of p-xylene conducted at a temperature of 225° C. and a gauge pressure of 26 kg/cm$^2$ using an acetic acid (4.3 weight percent water) to xylene weight ratio of 2:1 there are used for each 1.0 gram mole, 1.06 milligram atoms of cobalt, 3.07 milligram atoms of manganese and 2.68 milligram atoms of bromine.

The fluid oxidation effluent from any of the foregoing oxidations is a suspension of crystalline terephthalic acid in acetic acid solution of some terephthalic acid, catalyst components, and aromatic oxygen-containing co- and by-products and water. Some of the 4-CBA and even p-toluic acid are occluded in the terephthalic acid crystals. But the subsequent higher temperature dissolution puts all of the terephthalic acid and said co- and by-products into solution.

Whether the oxidation effluent need be diluted with fresh acetic acid to insure sufficient solvent for complete dissolution of all the solids depends upon the final solution temperature and the ratio of solids to solvent. The latter is dependent upon the weight ratio of acetic acid solvent to xylene used in the oxidation and is not effected to any appreciable extent by the water content of the acetic acid solvent over the range of 3 to 20 weight percent water and 97 to 80 weight percent acetic acid. Best commercial practice of the oxidation conducted in the acetic acid reaction solvent starts with a water content of 3 to 5 weight percent and controls the water content of the reaction solvent throughout the oxidation to the 3 to 5 weight percent range by drawing-off by-product water. However, accumulating all the by-product water results in the reaction solvent portion of the oxidation effluent having only 4.6 weight percent water starting with 3 weight percent water and a solvent to xylene ratio of 10:1 and having a 16.4 weight percent water starting with 3 weight percent water and a solvent to xylene ratio of 2:1. Any fresh solvent to be used can have the 3 to 20 weight percent water content but preferably has a water content of from 3 to 5 weight percent.

To dissolve all the solids at a temperature of from 260° C. up to 320° C. requires a pressure to maintain the solution in the liquid phase but gauge pressures of from 28 up to 70 kg/cm$^2$ can be used. At such temperature and pressure conditions the use of solvent to xylene weight ratios of from 1:1 to 7:1 requires the use of fresh acetic acid to dilute the oxidation effluent because at those conditions there is needed from 6 to 10 parts of solvent per 1.0 weight part solids to be dissolved. At oxidation, solvent to xylene weight ratios of 8:1 to 10:1, no fresh solvent is needed to dissolve the total solids present in the oxidation effluent. By "total solids" is meant the weight of solids which would be obtained upon removal of all acetic acid and water from the oxidation effluent and not only the solids suspended in the oxidation solvent.

The amount of hydrogen to be used is not critical and can be varied within the partial pressure range of 1.0 kg/cm$^2$ up to 14 kg/cm$^2$ absolute calculated at 20° C. and 0 gauge pressure.

For a fluid flow system, for example, the percolation of solution and hydrogen through a bed of supported metal hydrogenation catalyst, a residence time in the bed of from 5 to 10 minutes will be sufficient to reach reduction equilibrium conditions.

The preferred catalyst contains from 0.2 up to 2.0 weight percent palladium or platinum on the solid support of high surface area.

After the solution has been separated from the catalyst, cooling of the solution can be accomplished in any manner but flash evaporation of solvent in two or more preferably 3 to 5 steps in series can be advantageously used with heat energy conservation techniques. Such solute precipitation techniques by flash solvent evaporation are well known and present no known design problems.

The enabling practice of the present invention follows the practice of the illustrative examples next presented.

EXAMPLE 1

A fluid oxidation effluent produced from the air oxidation of p-xylene in the presence of acetic acid having 5 weight percent water (95 weight percent acetic acid) containing 0.5 milligram atoms of cobalt, 1.5 milligram atoms of manganese and 2.8 milligram atoms of bromine are continuously charged into a stirred-tank type oxidation vessel closed except for inlets for continuous charging of said liquids, continuous charging and return of condensate of exhaust vapors and outlets for the reaction's exhaust (nitrogen, unused oxygen, water vapor, acetic acid vapor and oxides of carbon) containing about 3 volume percent oxygen and the overflow of oxidation effluent. The weight ratio of said acetic acid solution to p-xylene feeds is 3:1. The oxidation reaction is conducted at a gauge pressure of 28 kg/cm$^2$ and a temperature of 225° C. Such reaction conditions produce an oxidation effluent containing 32.5 weight percent total solids.

A 400-gram sample of said fluid oxidation effluent is taken, cooled to 100° C. and filtered. The resulting filter cake is washed with acetic acid (1:1 weight ratio), dried and analyzed for 4-CBA. The partially purified terephthalic acid, 130 grams, is found to contain 0.26 weight percent 4-CBA.

A second 400-gram sample of the oxidation effluent is taken and diluted with hot (225° C.) 890 grams of 95 percent acetic acid (5 percent water). The resulting mixture containing 10 weight percent total solids is charged to an autoclave fitted with a stirrer and charged with hydrogen to the gauge pressure of 7 kg/cm$^2$. The diluted oxidation effluent is stirred and heated to the temperature of 285° C. and gauge pressure of 50 kg/cm$^2$. The autoclave is also fitted with a mesh catalyst basket which can be raised above or lowered into the liquid contents. Before sealing the autoclave there is placed 5.5 grams of particulate catalyst comprising 0.5 weight percent metallic palladium dispsersed on high surface per unit weight activated carbon support. The catalyst is lowered into the hot stirred liquid, and left therein for 100 minutes and then raised out of the liquid to separate catalyst therefrom. The contents of the autoclave are cooled to 25° C. The suspension at the temperature of 25° C. is filtered to collect the terephthalic acid precipitate which is then washed with fresh acetic acid (1:1 weight ratio) and dried.

COMPARATIVE EXAMPLE

For purposes of comparison, the 130 grams of partially purified terephthalic acid obtained from the first sample of oxidation effluent is combined with 1,160 grams of deionized water (sufficient to dissolve the solids at 285° C.), charged to an autoclave as above described having 5.5 grams of the 0.5 weight percent metallic palladium supported on the high area/weight activated carbon support and precharged with hydrogen (measured at 20° C.) to the gauge pressure of 7 kg/cm$^2$. Thereafter the fluid mixture and gas are stirred and heated to the temperature of 285° C. and a gauge pressure of 69 kg/cm$^2$. Then, while maintaining the 285° C. temperature, the catalyst basket is lowered into the hot stirred liquid, left therein for 100 minutes and then removed therefrom as before. The autoclave contents are cooled first to 100° C., the residual gas-vapor mixture vented and then cooled to 20°-25° C. The coold suspension of precipitated terephthalic acid in water is filtered to recover the filtrate as a filter cake. The filter cake is washed with water (1:1 weight ratio) and dried.

The foregoing two purified terephthalic acid products, upon analysis, are found to have the following properties:

| Product | 4-CBA Content | b-Color Value | p-toluic Acid Content |
|---|---|---|---|
| Example 1 | 0.0042 wt. % | 0.95 | 0.0004 wt. % |
| Comparative Example | 0.0010 wt. % | 1.1 | 0.0530 wt. % |

To be acceptable as fiber-grade quality terephthalic acid, such product should have a 4-CBA content below 0.01 and preferably below 0.005 weight percent.

The purification process of British Pat. No. 1,056,319 using hydrogen but no catalyst other than the cobalt and/or manganese inherently present in the oxidation effluent decreases the 4-CBA content of terephthalic acid product by 91 percent from 0.41 to 0.041 weight percent. But the present process according to Example 1 decreases the 4-CBA content by 98.4 percent.

The following examples are presented as guides for the preparation of other oxidation effluents containing impure terephthalic acid and their dilution when necessary prior to dissolving all of the total solids and the solution temperature therefore.

EXAMPLE 2

The fluid oxidation effluent is obtained by the simultaneous introduction of 68 kg p-xylene and air into an oxidation zone containing 160 kg of acetic acid (3 percent water) solution which has a bromine content of 0.23 weight percent, a cobalt content of 0.085 weight percent and a manganese content of 0.85 weight percent. The acetic acid solution is at the temperature of 205° C. and the gauge pressure of 22.5 kg/cm$^2$. The xylene is introduced over a period of 45 minutes and the air rate is 3.289$^3$/kg of p-xylene. The reaction is terminated then minutes after all the xylene is charged. The fluid oxidation effluent amounts to 262 kg and has a total solids content of 38.7 weight percent.

The oxidation effluent is pumped into a closed, stirred dissolving tank and 419 kg of 97 percent acetic acid is also pumped into the effluent transfer line going to the dissolving tank which has a pressure control valve set at 42.2 kg/cm$^2$ gauge pressure. The diluted oxidation effluent has an acetic acid content of 97 weight percent (3 weight percent water) and has 5.3 weight parts of said acetic acid per weight part of total solids which is sufficient solvent to dissolve all the total solids at the temperature of 282° C. Accordingly, the diluted effluent is stirred and heated to the temperature of 282° C.

At said temperature and 42.2 kg/cm$^2$ gauge pressure the resulting solution is pumped into the top of a reaction vessel operated at 47.8 kg/cm$^2$ gauge pressure, containing a bed of 0.5 weight percent Pd disposed on particulate activated carbon having a surface area per gram ratio of 2,500:1.0. Hydrogen gas (7 kg/cm$^2$ partial pressure) is added to the solution before it enters the reactor. The solution and dissolved hydrogen percolate through the bed of catalyst which is of sufficient size to provide a solution contact time with the catalyst of 5 to 10 minutes before the treated solution and unused hydrogen enters a gas disengaging zone from which a mixture of hydrogen gas and acetic acid vapors are taken and pumped into the top of the reaction vessel. The degassed solution separated from the catalyst is then cooled in four steps by flash evaporation of acetic acid at successively lower pressures to a final gauge pressure of 0.7 kg/cm$^2$.

The resulting suspension of precipitated terephthalic acid is charged to a centrifugal filter, the collected precipitate is washed with fresh 97 percent acetic acid and dried. In the foregoing manner fiber-grade terephthalic acid having less than 0.005 weight percent 4-CBA, less than 0.001 weight percent p-toluic acid and a b-color value below 1.0 can be obtained.

EXAMPLE 3

A continuous oxidation of p-xylene is conducted at the temperature of 220° C., under a gauge pressure of 28.2 kg/cm$^2$ and using a weight ratio of 96.5 percent acetic acid (3.5 percent water) to p-xylene of 10:1. No water by-product is removed during the reaction. There are produced 594 kg/hr of fluid oxidation effluent having a total solids content of 12.5 weight percent. There are present 14.28 kg total solids for each 100 kg of acetic acid solvent (93.3 percent acetic acid and 6.7 percent water by weight) in the effluent. Such amount of solvent is adequate to dissolve all the total solids at the temperature of 271° C. without the addition of fresh acetic acid.

Said oxidation effluent is, therefore, heated to 271° C. from 220° C. together with 7 kg/cm$^2$ partial pressure hydrogen gas under a gauge pressure of 36 kg/cm$^2$. The mixture of solution and hydrogen is percolated from the top to the bottom of a catalyst bed as described in Example 2 of a bed size to provide a contact time with the catalyst of 5 to 10 minutes. After separation of solution from catalyst and degassing the solution to remove unused hydrogen, the solution is decompressed in three successive steps of decreasing pressure to a final gauge pressure of 0.5 kg/cm$^2$. The solvent flash evaporated in each step is removed. The final suspension of terephthalic acid precipitate is fed to a rotating drum vacuum filter to separate the precipitate from mother liquor and collect the precipitate so that it can be washed with fresh acetic acid. The washed cake of collected precipitate is removed from the drum and dried.

Fiber-grade terephthalic acid can be obtained by the process of Example 3.

EXAMPLE 4

Again p-xylene is oxidized continuously but at the temperature of 232° C. under a gauge pressure of 29.5 kg/cm$^2$ using a weight ratio of 1:1 of 98.8 percent acetic acid (1.2 percent water) to p-xylene. By this oxidation 268 kg/hr of oxidation effluent containing 51.4 percent total solids and 26.2 percent water by weight. As such, fluid oxidation effluent is transferred first to a surge tank diluted in the transfer line with 644 kg/hr of 100 percent acetic acid. Some vapors are purged from the surge tank to remove dissolved oxygen. Then the oxygen free diluted effluent containing 773.4 kg/hr of acetic acid solvent is transferred to the dissolver before described. The solvent contains 4.8 percent water and 95.2 percent acetic acid by weight. Such amount of said solvent is sufficient to dissolve the 137.8 kg/hr of the total solids entering the dissolver at the dissolving temperature of 283° C. Hydrogen gas is also injected in the transfer line leading to the dissolver which is operated under a gauge pressure of 47.8 kg/cm$^2$ and a temperature of 283° C. The hydrogen partial pressure is 7 kg/cm$^2$.

The mixture of solution and hydrogen is fed to the top of a reactor containing a bed of 0.5 weight percent palladium on activated carbon (3,000 m$^2$/g) of sufficient quantity to provide a catalyst contact time of 5 to 10 minutes. After separation from catalyst and having its unused hydrogen removed, the treated solution is decompressed in five sequential steps to flash evaporate solvent to a final gauge pressure of 0 kg/cm$^2$. The resulting suspension of precipitated terephthalic acid is gravity fed to a vacuum drum filter for separation of mother liquor from precipitate and its collection on the drum for washing with fresh acetic acid.

The dried terephthalic acid product from the foregoing example will be of fiber-grade quality.

The invention claimed is:

1. A process for the recovery of terephthalic acid of fiber-grade quality directly from the fluid effluent obtained (a) by catalytically oxidizing p-xylene in the liquid phase at a temperature from 170° C. to 225° C. with air as the source of oxygen and in the presence for 1.0 weight part of p-xylene from 2.0 to 10 weight parts of an acetic acid solution as the reaction solvent containing 0.4 to 22 milligram atoms of cobalt per 1.0 gram mole of p-xylene for each milligram atom of cobalt from 0.05 to 2.0 milligram atoms of manganese and for each milligram atom of total cobalt and manganese from 0.5 up to 1.5 milligram atoms of bromine; (b) heating the resulting fluid oxidation effluent comprising about 3 to 20 weight percent water and about 97 to 80 weight percent acetic acid to a temperature of from 260° C. up to 320° C. under a pressure sufficient to maintain a liquid phase of acetic acid and in the presence of sufficient acetic acid to dissolve all solids present in said effluent at the temperature range of 260° C. to 320° C. ; (c) contacting the resulting solution and with hydrogen gas in the amount to provide its partial pressure of from 1.0 up to 15 kg/cm$^2$ with a platinum family metal catalyst; (d) cooling the hydrogen treated solution to precipitate terephthalic acid therefrom; (e) separating the precipitate from the acetic acid mother liquor; comprising about 97 to 80 weight percent acetic acid, and about 3 to 20 weight percent water; (f) washing the separated precipitate with fresh acetic acid; comprising about 3 to about 20 weight percent water and about 97 to about 80 weight percent acetic acid; and (g) drying the washed precipitate.

2. The process of claim 1 wherein the platinum family metal catalyst is platinum or palladium metal supported on the surface of an insoluble support.

3. The process of claim 2 wherein the platinum family metal catalyst is 0.2 up to 2.0 weight percent palladium supported on the surface of an insoluble support.

4. The process of claim 3 wherein the insoluble support is activated carbon having a ratio of surface area per unit weight in the range of from 1,000:1 up to 3,000:1.

5. The process of claim 4 wherein the amount of acetic acid present in the heating step is from 6 to 10 weight parts per 1.0 weight part of total solids present and the time of contact of the resulting solution with the supported metal catalyst is from 5 up to 10 minutes.

6. The process of claim 5 wherein the cooling of the catalytically hydrogenated solution is conducted by flash evaporation of acetic acid solvent at sequentially lower pressures in at least two steps to a final pressure down to 0.5 kg/cm$^2$ gauge pressure.

7. The process of claim 6 wherein the sequential steps of flash evaporation of acetic acid solvent are from 2 up to 8 steps.

8. The process of claim 7 wherein the sequential steps of flash evaporation of acetic acid solvent is from 2 to 5 steps.

9. A process for the recovery of terephthalic acid of fiber-grade quality directly from the fluid effluent obtained (a) by catalytically oxidizing p-xylene in the liquid phase at a temperature from 170° C. to 225° C. with air as the source of oxygen and in the presence for 1.0 weight part of p-xylene from 2.0 to 10 weight parts of an acetic acid solution as the reaction solvent containing 0.4 to 22 milligram atoms of cobalt per 1.0 gram mole of p-xylene for each milligram atom of cobalt from 0.05 to 2.0 milligram atoms of manganese and for each milligram atom of total cobalt and manganese from 0.5 up to 1.5 milligram atoms of bromine; (b) heating the resulting fluid oxidation effluent comprising about 3 to 5 weight percent water and about 97 to about 95 weight percent acetic acid to a temperature of from 260° C. up to 320° C. under a pressure sufficient to maintain a liquid phase of acetic acid and in the presence of sufficient acetic acid to dissolve all solids present in said effluent at the temperature range of 260° C. to 320° C.; (c) contacting the resulting solution with hydrogen gas in the amount to provide its partial pressure of from 1.0 up to 15 kg/cm$^2$ with a platinum family metal catalyst; (d) cooling the hydrogen treated solution to precipitate terephthalic acid therefrom; (e) separating the precipitate from the acetic acid mother liquor comprising about 97 to 95 weight percent acetic acid and about 3 to 5 weight percent water; (f) washing the separated precipitate with fresh acetic acid comprising about 3 to about 5 weight percent water and about 97 to about 95 weight percent acetic acid; and (g) drying the washed precipitate.

* * * * *